United States Patent
Muneyasu

(10) Patent No.: US 11,046,634 B2
(45) Date of Patent: Jun. 29, 2021

(54) HIGH-PURITY CARBOXYLIC ACID ESTER AND METHOD FOR PRODUCING SAME

(71) Applicant: MITSUBISHI GAS CHEMICAL COMPANY, INC., Tokyo (JP)

(72) Inventor: Kuniaki Muneyasu, Niigata (JP)

(73) Assignee: MITSUBISHI GAS CHEMICAL COMPANY, INC., Tokyo (JP)

( * ) Notice: Subject to any disclaimer, the term of this patent is extended or adjusted under 35 U.S.C. 154(b) by 0 days.

(21) Appl. No.: 16/565,767

(22) Filed: Sep. 10, 2019

(65) Prior Publication Data

US 2020/0002264 A1 Jan. 2, 2020

Related U.S. Application Data

(62) Division of application No. 15/763,590, filed as application No. PCT/JP2016/078379 on Sep. 27, 2016, now abandoned.

(30) Foreign Application Priority Data

Oct. 2, 2015 (JP) .............................. JP2015-196769

(51) Int. Cl.
| | | |
|---|---|---|
| *C07C 67/56* | (2006.01) | |
| *B01J 41/07* | (2017.01) | |
| *C07C 69/68* | (2006.01) | |
| *B01J 39/26* | (2006.01) | |
| *B01J 41/20* | (2006.01) | |
| *B01J 47/028* | (2017.01) | |

(52) U.S. Cl.
CPC ............... *C07C 67/56* (2013.01); *B01J 39/26* (2013.01); *B01J 41/07* (2017.01); *B01J 41/20* (2013.01); *B01J 47/028* (2013.01); *C07C 69/68* (2013.01)

(58) Field of Classification Search
CPC ....... C07C 67/56; C07C 69/68; C07C 69/675; B01J 41/07; B01J 39/05; B01J 39/26; B01J 41/20; B01J 47/028; A44B 19/262; A44B 19/301; A44B 19/308
See application file for complete search history.

(56) References Cited

U.S. PATENT DOCUMENTS

| | | | |
|---|---|---|---|
| 6,123,850 A | 9/2000 | Commarieu et al. | |
| 6,642,350 B1 | 11/2003 | Asakawa et al. | |
| 7,306,738 B2* | 12/2007 | Inada | C07C 67/56 |
| | | | 210/664 |
| 2005/0096481 A1* | 5/2005 | Hildebrandt | C07C 67/08 |
| | | | 560/55 |

FOREIGN PATENT DOCUMENTS

| | | |
|---|---|---|
| CN | 102320969 | 1/2012 |
| CN | 102381973 | * 3/2012 |
| CN | 104610061 | * 5/2015 |
| CN | 105037156 | * 11/2015 |
| CN | 105037156 A | 11/2015 |
| JP | 54-157504 | 12/1979 |
| JP | 61-207345 | 9/1986 |
| JP | 8-283202 | 10/1996 |
| JP | 10-316594 | 12/1998 |
| JP | 2004-181351 | 7/2004 |
| JP | 2004-181352 | 7/2004 |
| JP | 2005-247770 | 9/2005 |
| JP | 3813199 | 6/2006 |
| JP | 2007-117781 | 5/2007 |
| JP | 4116104 | 4/2008 |
| JP | 4302201 | 5/2009 |
| JP | 2009-155208 | 7/2009 |

OTHER PUBLICATIONS

CN105037156 translated (Year: 2015).*
Amberlite one page (Year: 2012).*
CN102381973 translated (Year: 2012).*
Rohm and Haas two pages (Year: 2008).*
CN104610061 trnslated (Year: 2015).*
Official Communication for PCT/JP2016/078379, dated Dec. 27, 2016.
Nutrivita, pp. 1-8, Published 2011 (Year: 2011) *Cited on Oct. 11, 2018 PTO-892 in parent U.S. Appl. No. 15/763,590.

* cited by examiner

*Primary Examiner* — Yevgeny Valenrod
*Assistant Examiner* — Blaine G Doletski
(74) *Attorney, Agent, or Firm* — Greenblum & Bernstein, P.L.C.

(57) ABSTRACT

A method for producing a high-purity carboxylic acid ester, the method including bringing a crude carboxylic acid ester that contains anionic impurities and Ag, Al, Au, Ca, Cr, Cu, Fe, K, Mg, Na, Sn, and Zn metal impurities into contact with a cation-exchange resin, followed by bringing the crude carboxylic acid ester into contact with an anion-exchange resin to obtain to provide a high-purity carboxylic acid ester in which the Ag, Al, Au, Ca, Cr, Cu, Fe, K, Mg, Na, Sn, and Zn metal impurity content are each less than 1 ppb and the anionic impurity content is less than 1 ppm.

9 Claims, 1 Drawing Sheet

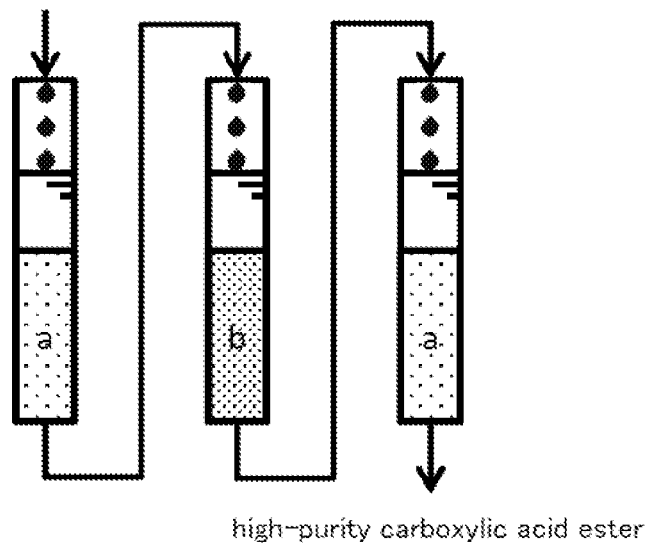

HIGH-PURITY CARBOXYLIC ACID ESTER AND METHOD FOR PRODUCING SAME

CROSS-REFERENCE TO RELATED APPLICATIONS

This application is a Divisional of U.S. application Ser. No. 15/763,590, which is a National Stage of PCT/JP2016/078379, filed Sep. 27, 2016, which claims priority to JP App. No. 2015-196769, filed Oct. 2, 2015. Each of the above applications is incorporated by reference herein in its entirety.

TECHNICAL FIELD

The present invention relates to a method for purifying a carboxylic acid ester, wherein the metal impurity content and the anionic impurity content are reduced. The carboxylic acid ester of the present invention is useful for a wide range of applications such as synthetic raw materials, cleaning agents for electronic components and solvents for paints, adhesives and the like. Further, it is used as a treatment agent for cleaning of a semiconductor substrate, etching, development of a photoresist and the like in the production of integrated circuits and large-scale integrated circuits. In particular, in applications for semiconductors, very high purity is required because of contamination of semiconductor substrates, and a high-purity carboxylic acid ester containing impurities in an amount as small as possible is required.

BACKGROUND ART

However, carboxylic acid esters conventionally used have high concentrations of metal impurities and anionic impurities, and have problems in which, for example, these cannot be used in applications for semiconductors.

For example, Patent Document 1 describes a method for limiting the water content in a carboxylic acid ester as a technique for improving storage stability and corrosiveness against metal materials of the carboxylic acid ester. Further, the document describes a method for limiting the water content to suppress hydrolysis of the carboxylic acid ester, thereby suppressing increase in an acid content (a hydrolyzate of the carboxylic acid ester) which causes corrosion of metal materials, etc., but does not describe reduction in metal impurities.

Patent Document 2 describes a method for reducing an acid content in a carboxylic acid ester by means of neutralization or the like to improve storage stability (decomposition, discoloration, etc. during storage). In this method, just decomposition and discoloration of the carboxylic acid ester itself are suppressed, and the document does not describe reduction in metal impurities.

Patent Document 3 describes a method for bringing a substantially anhydrous organic solution into contact with one or a plurality of cation-exchange resins for the purpose of reducing the content of alkali metal and alkaline earth metal cations. In the document, the type of metal cations to be reduced is limited to alkali metals and alkaline earth metals, and the document does not describe reduction in anionic impurities. Therefore, the method is insufficient as a method for purifying a carboxylic acid ester.

Patent Documents 4 and 5 describe a method of purification with a very high purity at the time of removing metal ions and the like contained in a non-aqueous liquid material using an ion exchange resin, wherein the non-aqueous liquid material is brought into contact with a cation-exchange resin alone or a mixed ion exchange resin consisting of a cation-exchange resin and an anion-exchange resin to reduce the concentration of metal impurities in the non-aqueous liquid material to a very low level, and wherein an eluate from the resin itself is also removed. However, the Na concentration after purification is 50 ppb or less and does not satisfy the concentration of metal impurities required for applications for semiconductors (1 ppb or less), and therefore the method is insufficient as a method for purifying a carboxylic acid ester.

Patent Document 6 describes a method of removing metal ions in an organic solvent by using an ion exchange resin having OH or a weak acid as a counter ion of a strongly basic anion-exchange resin. However, the document describes only Fe and Pd as metal impurities that can be removed, and does not describe removal of impurities including other alkali metals. Therefore, the method is insufficient as a method for purifying a carboxylic acid ester. Thus, there is no known method for highly purifying a carboxylic acid ester.

PRIOR ART DOCUMENTS

Patent Documents

Patent Document 1: Japanese Patent No. 3813199
Patent Document 2: Japanese Patent No. 4116104
Patent Document 3: Japanese Patent No. 4302201
Patent Document 4: Japanese Laid-Open Patent Publication No. 2004-181351
Patent Document 5: Japanese Laid-Open Patent Publication No. 2004-181352
Patent Document 6: Japanese Laid-Open Patent Publication No. 2005-247770

SUMMARY OF THE INVENTION

Problems to be Solved by the Invention

The objective of the present invention is to provide a high-purity carboxylic acid ester, wherein the metal impurity content and the anionic impurity content are significantly reduced.

Means for Solving the Problems

The present inventors diligently made researches on methods for purifying a carboxylic acid ester in order to solve the problems and found that a carboxylic acid ester can be highly purified by using an ion exchange resin at the time of removing metal impurities and anionic impurities from carboxylic acid ester and by defining the order of a cation-exchange resin and anion-exchange resin for flowing through, and thus the present invention was achieved.

Specifically, the present invention is as follows:
<1> A high-purity carboxylic acid ester, wherein the Ag, Al, Au, Ca, Cr, Cu, Fe, K, Mg, Na, Sn and Zn contents as metal impurity contents are each less than 1 ppb, and wherein the anionic impurity content is less than 1 ppm.
<2> A method for producing a high-purity carboxylic acid ester, the method including: a step of bringing a crude carboxylic acid ester that contains anionic impurities and at least Ag, Al, Au, Ca, Cr, Cu, Fe, K, Mg, Na, Sn and Zn as metal impurities into contact with a cation-exchange resin (II); and a step of subsequently bringing the crude carboxylic acid ester into contact with an anion-exchange resin (III).

<3> The method for producing a high-purity carboxylic acid ester according to item <2>, which includes a step of bringing the crude carboxylic acid ester into contact with an anion-exchange resin (I) before bringing the crude carboxylic acid ester into contact with the cation-exchange resin (II).

<4> The method for producing a high-purity carboxylic acid ester according to item <2> or <3>, wherein the carboxylic acid ester is at least one selected from the group consisting of methyl lactate, ethyl lactate, propyl lactate, methyl α-hydroxyisobutyrate, ethyl α-hydroxyisobutyrate, propyl α-hydroxyisobutyrate, butyl α-hydroxyisobutyrate, methyl β-hydroxyisobutyrate, ethyl β-hydroxyisobutyrate, propyl β-hydroxyisobutyrate and butyl β-hydroxyisobutyrate.

<5> The method for producing a high-purity carboxylic acid ester according to any one of items <2> to <4>, wherein in the obtained high-purity carboxylic acid ester, the Ag, Al, Au, Ca, Cr, Cu, Fe, K, Mg, Na, Sn and Zn contents as metal impurity contents are each less than 1 ppb and the anionic impurity content is less than 1 ppm.

<6> The method for producing a high-purity carboxylic acid ester according to any one of items <2> to <5>, wherein in the crude carboxylic acid ester, the Ag, Al, Au, Ca, Cr, Cu, Fe, K, Mg, Na, Sn and Zn contents as metal impurity contents are each 8 ppb or more and the anionic impurity content is 20 ppm or more.

Advantageous Effect of the Invention

In the high-purity carboxylic acid ester obtained by the method of the present invention, metal impurities and anionic impurities are highly reduced, and it can be suitably used for many applications in which a carboxylic acid ester is used, in particular, applications in the field of electronics industry. Specifically, it is used for a wide range of applications such as synthetic raw materials, cleaning agents for electronic components and solvents for paints, adhesives and the like, or it is used as a treatment agent for cleaning of a semiconductor substrate, etching, development of a photoresist and the like in the production of integrated circuits and large-scale integrated circuits. Accordingly, the present invention has industrial significance.

BRIEF DESCRIPTION OF THE DRAWINGS

The FIG. 1 is a schematic view showing a process of obtaining a high-purity carboxylic acid ester by flowing a carboxylic acid ester through a weakly basic anion-exchange resin (I), a strongly acidic cation-exchange resin (II) and a weakly basic anion-exchange resin (III) in this order in Examples 1 and 2.

EMBODIMENT FOR CARRYING OUT THE INVENTION

Hereinafter, the present invention will be described in detail. The present invention relates to a high-purity carboxylic acid ester in which metal impurity contents are each less than 1 ppb and the anionic impurity content is less than 1 ppm, and a method for producing the same.

The high-purity carboxylic acid ester of the present invention is produced by bringing a crude carboxylic acid ester that contains metal impurities and anionic impurities into contact with a cation-exchange resin and an anion-exchange resin to remove the metal impurities with both the cation-exchange resin and the anion-exchange resin and remove the anionic impurities with the anion-exchange resin. Examples of the anionic impurities of the present invention include a carboxylic acid, which is contained in the crude carboxylic acid ester and is generated by a hydrolysis reaction of the carboxylic acid ester.

The crude carboxylic acid ester of the present invention contains metal impurities and anionic impurities. It may also contain water as one of other components. Examples of the metal impurities include at least Ag, Al, Au, Ca, Cr, Cu, Fe, K, Mg, Na, Sn and Zn. In the crude carboxylic acid ester of the present invention, the Ag, Al, Au, Ca, Cr, Cu, Fe, K, Mg, Na, Sn and Zn contents as the contents of the metal impurities are each preferably 8 ppb or more. Further, the content of the anionic impurities is preferably 20 ppm or more. According to the present invention, it is possible to produce a high-purity carboxylic acid ester even when using such a crude carboxylic acid ester with a high impurity concentration.

As the cation-exchange resin (II) to be used in the present invention, an H-type strongly acidic cation-exchange resin and a Na-type strongly acidic cation-exchange resin are preferred, and among them, an H-type strongly acidic cation-exchange resin having a sulfonic acid group can be particularly suitably used. As the above-described cation-exchange resin, a commercially-available product can be used, and specific examples thereof include 15JS-HG DRY (manufactured by Organo Corporation).

In the present invention, as described later, there are: 1. a method of bringing a crude carboxylic acid ester into contact with a cation-exchange resin and then with an anion-exchange resin; and 2. a method of bringing a crude carboxylic acid ester into contact with an anion-exchange resin, then with a cation-exchange resin, and then with an anion-exchange resin. Hereinafter, the anion-exchange resin that is contacted after contact with the cation-exchange resin is sometimes referred to as an anion-exchange resin (III), and the anion-exchange resin that is contacted before contact with the cation-exchange resin is sometimes referred to as an anion-exchange resin (I).

Examples of the anion-exchange resins (I) and (III) to be used in the present invention include a strongly basic anion-exchange resin and a weakly basic anion-exchange resin, but a weakly basic anion-exchange resin is preferred, and a free base type weakly basic anion-exchange resin is more preferred. Among them, a weakly basic anion-exchange resin having a tertiary ammonium base can be particularly suitably used. As the above-described anion-exchange resin, a commercially-available product can be used, and specific examples thereof include B20-HG DRY (manufactured by Organo Corporation). In the present invention, the anion-exchange resin (I) and the anion-exchange resin (III) may be the same or different.

In the present invention, the method for bringing the crude carboxylic acid ester into contact with the cation-exchange resin (II) and anion-exchange resins (I) and (III) is not particularly limited, but a method for flowing the crude carboxylic acid ester through the cation-exchange resin and anion-exchange resins is generally employed. Regarding the temperature conditions at the time of contact, in consideration of durability of ion exchange resins, the temperatures of the crude carboxylic acid ester, cation-exchange resin and anion-exchange resins are preferably 100° C. or lower. Further, the production method of the present invention can be carried out by using either a batch method or a flow method, but in view of purification efficiency, the flow method in which the crude carboxylic acid ester is flowed through columns filled with ion exchange resins is preferably employed. When purification is performed using the flow method, the method of delivering a solution may be either upflow or downflow, and the space velocity of flowing through (SV: $Hr^{-1}$) is suitably determined depending on the type and viscosity of the solution, pressure loss of resin, etc. but is preferably 1 to 50 $Hr^{-1}$, and more preferably 10 to 20 $Hr^{-1}$. The concentration of moisture in the crude carboxylic acid ester is not defined, but when bringing a carboxylic acid ester containing moisture into contact with the cation-exchange resin and flowing it therethrough, an acid content is generated by hydrolysis. When subsequently bringing the carboxylic acid ester containing the increased acid content into contact with the anion-exchange resin and flowing it therethrough, the generated acid content is captured by the anion-exchange resin and shortens the life of the anion-exchange resin. For this reason, the concentration of moisture in the crude carboxylic acid ester is preferably 0.01% by weight or less.

As the method for producing the high-purity carboxylic acid ester of the present invention, a method in which contact with the anion-exchange resin (I) is performed before contact with the cation-exchange resin (II) is more preferred. When bringing the crude carboxylic acid ester into contact with the cation-exchange resin (II), as described above, the hydrolysis reaction between moisture contained in the crude carboxylic acid ester and the carboxylic acid ester is caused to newly generate the anionic impurities. According to the above-described method, the anionic impurities (the carboxylic acid) contained in the crude carboxylic acid ester are brought into contact with the anion-exchange resin (I) to be captured before contact with the cation-exchange resin (II), thereby reducing the load of the anionic impurities to be subsequently captured by the anion-exchange resin (III). For this reason, the life of the anion-exchange resin (III) can be improved.

EXAMPLES

Hereinafter, the present invention will be specifically described by way of working examples and comparative examples. However, the present invention is not limited to the working examples. Note that the concentrations of the metal impurities and anionic impurities in the carboxylic acid ester were analyzed as described below.
<Analysis of Concentration of Metal Impurities>
Quantitative analysis was carried out using an ICP mass spectrometer (Agilent 7900 ICP-MS manufactured by Agilent).
<Analysis of Concentration of Anionic Impurities>
Quantitative analysis was carried out using an automatic titrator (automatic titrator AT-510 manufactured by Kyoto Electronics Manufacturing Co., Ltd.) with 0.01 mol/L of sodium hydroxide. Analysis was carried out after 30 mL of methanol was added to 50 mL of carboxylic acid ester.

Example 1

As a pretreatment, each of an H-type strongly acidic cation-exchange resin (trade name: 15JS-HG DRY, manufactured by Organo Corporation) and a free base type weakly basic anion-exchange resin (trade name: B20-HG DRY, manufactured by Organo Corporation) was put into ethyl lactate separately and immersed therein for 1 hour or longer while being gently stirred suitably. After that, one FEP column having an inner diameter of 16 mm was filled with 10 ml of strongly acidic cation-exchange resin, and each of two FEP columns having an inner diameter of 16 mm was filled with 10 ml of weakly basic anion-exchange resin. After that, ethyl lactate was flowed through the weakly basic anion-exchange resin (I), the strongly acidic cation-exchange resin (II) and the weakly basic anion-exchange resin (III) in this order at 25° C. with SV=20 $Hr^{-1}$ as shown in the FIG. Respective concentrations of impurities after flowing through are shown in Table 1. From Table 1, it is understood that all the metal and anion contents described therein were highly removed.

Example 2

As a pretreatment, each of an H-type strongly acidic cation-exchange resin (trade name: 15JS-HG DRY, manufactured by Organo Corporation) and a free base type weakly basic anion-exchange resin (trade name: B20-HG DRY, manufactured by Organo Corporation) was put into methyl hydroxyisobutyrate separately and immersed therein for 1 hour or longer while being gently stirred suitably. After that, one FEP column having an inner diameter of 16 mm was filled with 10 ml of strongly acidic cation-exchange resin, and each of two FEP columns having an inner diameter of 16 mm was filled with 10 ml of weakly basic anion-exchange resin. After that, methyl hydroxyisobutyrate was flowed through the weakly basic anion-exchange resin (I), the strongly acidic cation-exchange resin (II) and the weakly basic anion-exchange resin (III) in this order at 25° C. with SV=20 $Hr^{-1}$ as shown in the FIG. Respective concentrations of impurities after flowing through are shown in Table 2. From Table 2, it is understood that all the metal and anion contents described therein were highly removed.

Further, the amount of methyl hydroxyisobutyrate flowed through was increased. The anionic impurity concentrations after flowing through are shown in Table 3. According to Table 3, the anion content was highly removed during time between when flowing through was started and when the amount was 2000 ml, but the anion content was increased after the amount reached 2500 ml.

Example 3

An H-type strongly acidic cation-exchange resin (trade name: 15JS-HG DRY, manufactured by Organo Corporation) and a free base type weakly basic anion-exchange resin (trade name: B20-HG DRY, manufactured by Organo Corporation) were pretreated with methyl hydroxyisobutyrate in a manner similar to that in Example 2. After that, one FEP column having an inner diameter of 16 mm was filled with 10 ml of strongly acidic cation-exchange resin, and another FEP column having an inner diameter of 16 mm was filled with 10 ml of weakly basic anion-exchange resin. After that, methyl hydroxyisobutyrate was flowed through the strongly acidic cation-exchange resin (II) and the weakly basic anion-exchange resin (III) in this order at 25° C. with SV=20 $Hr^{-1}$. Respective concentrations of impurities after flowing through are shown in Table 4. From Table 4, it is understood that all the metals described therein were highly removed. The anion content was highly removed during time between when flowing through was started and when the amount was 1500 ml, but the anion content was increased after the amount reached 1500 ml.

According to the results of Examples 2 and 3, the ability to remove the anion content can be more improved in Example 2 in which methyl hydroxyisobutyrate was flowed through the weakly basic anion-exchange resin (I) before it was flowed through the strongly acidic cation-exchange resin (II), and in addition, the life of the anion-exchange resin (III) can be improved.

Comparative Example 1

An H-type strongly acidic cation-exchange resin (trade name: 15JS-HG DRY, manufactured by Organo Corporation) was pretreated with ethyl lactate in a manner similar to that in Example 1. After that, an FEP column having an inner diameter of 16 mm was filled with 20 ml of strongly acidic cation-exchange resin, and after that, ethyl lactate was flowed therethrough at 25° C. with SV=20 $Hr^{-1}$. Respective concentrations of impurities after flowing through are shown in Table 5. From Table 5, it is understood that Ag, Au, Cr, Fe and Sn were hardly removed, and that it was impossible to remove the anionic impurities.

Comparative Example 2

A free base type weakly basic anion-exchange resin (trade name: B20-HG DRY, manufactured by Organo Corporation) was pretreated with ethyl lactate in a manner similar to that in Example 1. After that, an FEP column having an inner diameter of 16 mm was filled with 20 ml of free base type weakly basic anion-exchange resin, and after that, ethyl lactate was flowed therethrough at 25° C. with SV=20 $Hr^{1}$. Respective concentrations of impurities after flowing through are shown in Table 6. From Table 6, it is understood that K and Na were hardly removed.

Comparative Example 3

10 ml of an H-type strongly acidic cation-exchange resin (trade name: 15JS-HG DRY, manufactured by Organo Corporation) was mixed with 20 ml of a free base type weakly basic anion-exchange resin (trade name: B20-HG DRY, manufactured by Organo Corporation), and the mixture was pretreated with ethyl lactate in a manner similar to that in Example 1. After that, an FEP column having an inner diameter of 16 mm was filled with 30 ml of the mixture, and then ethyl lactate was flowed therethrough at 25° C. with SV=20 $Hr^{-1}$. Respective concentrations of impurities after flowing through are shown in Table 7. From Table 7, it is understood that Ca and Cr were insufficiently removed.

Comparative Example 4

An H-type strongly acidic cation-exchange resin (trade name: 15JS-HG DRY, manufactured by Organo Corporation) was pretreated with methyl hydroxyisobutyrate in a manner similar to that in Example 2. After that, an FEP column having an inner diameter of 16 mm was filled with 20 ml of strongly acidic cation-exchange resin, and after that, methyl hydroxyisobutyrate was flowed therethrough at 25° C. with SV=20 $Hr^{-1}$. Respective concentrations of impurities after flowing through are shown in Table 8. From Table 8, it is understood that Ag, Au, Fe and Sn were hardly removed, and that it was impossible to remove the anionic impurities.

Comparative Example 5

A free base type weakly basic anion-exchange resin (trade name: B20-HG DRY, manufactured by Organo Corporation) was pretreated with methyl hydroxyisobutyrate in a manner similar to that in Example 2. After that, an FEP column having an inner diameter of 16 mm was filled with 20 ml of the free base type weakly basic anion-exchange resin, and after that, methyl hydroxyisobutyrate was flowed therethrough at 25° C. with SV=20 $Hr^{-1}$. Respective concentrations of impurities after flowing through are shown in Table 9. From Table 9, it is understood that K and Na were hardly removed.

Comparative Example 6

10 ml of an H-type strongly acidic cation-exchange resin (trade name: 15JS-HG DRY, manufactured by Organo Corporation) was mixed with 20 ml of a free base type weakly basic anion-exchange resin (trade name: B20-HG DRY, manufactured by Organo Corporation), and the mixture was pretreated with methyl hydroxyisobutyrate in a manner similar to that in Example 2. After that, an FEP column having an inner diameter of 16 mm was filled with 30 ml of the mixture, and then methyl hydroxyisobutyrate was flowed therethrough at 25° C. with SV=20 $Hr^{-1}$. Respective concentrations of impurities after flowing through are shown in Table 10. From Table 10, it is understood that Ca and Cr were insufficiently removed.

TABLE 1

| Metallic element content (unit: ppb) | Before flowing through | After flowing through |
|---|---|---|
| Ag | 10 | <1 |
| Al | 10 | <1 |
| Au | 10 | <1 |
| Ca | 10 | <1 |
| Cr | 10 | <1 |
| Cu | 10 | <1 |
| Fe | 10 | <1 |
| K | 10 | <1 |
| Mg | 10 | <1 |
| Na | 10 | <1 |
| Sn | 10 | <1 |
| Zn | 10 | <1 |
| Anionic impurities (unit: ppm) | 30 | <1 |

TABLE 2

| Metallic element content (unit: ppb) | Before flowing through | After flowing through |
|---|---|---|
| Ag | 10 | <1 |
| Al | 10 | <1 |
| Au | 10 | <1 |
| Ca | 10 | <1 |
| Cr | 10 | <1 |
| Cu | 10 | <1 |
| Fe | 10 | <1 |
| K | 10 | <1 |
| Mg | 10 | <1 |
| Na | 10 | <1 |
| Sn | 10 | <1 |
| Zn | 10 | <1 |
| Anionic impurities (unit: ppm) | 30 | <1 |

TABLE 3

| Flow-through amount | Before flowing through | 500 ml | 1000 ml | 1500 ml | 2000 ml | 2500 ml |
|---|---|---|---|---|---|---|
| Anionic impurities (unit: ppm) | 30 | <1 | <1 | <1 | <1 | 10 |

TABLE 4

Metallic element content (unit: ppb)

| Element | Before flowing through | After flowing through |
|---|---|---|
| Ag | 10 | <1 |
| Al | 10 | <1 |
| Au | 10 | <1 |
| Ca | 10 | <1 |
| Cr | 10 | <1 |
| Cu | 10 | <1 |
| Fe | 10 | <1 |
| K  | 10 | <1 |
| Mg | 10 | <1 |
| Na | 10 | <1 |
| Sn | 10 | <1 |
| Zn | 10 | <1 |

| Flow-through amount | Before flowing through | 500 ml | 1000 ml | 1500 ml | 2000 ml | 2500 ml |
|---|---|---|---|---|---|---|
| Anionic impurities (unit: ppm) | 30 ppm | <1 ppm | <1 ppm | <1 ppm | 10 ppm | 20 ppm |

TABLE 5

| Metallic element content (unit: ppb) | Before flowing through | After flowing through |
|---|---|---|
| Ag | 10 | 10 |
| Al | 10 | 2 |
| Au | 10 | 10 |
| Ca | 10 | 2 |
| Cr | 10 | 10 |
| Cu | 10 | <1 |
| Fe | 10 | 10 |
| K  | 10 | <1 |
| Mg | 10 | <1 |
| Na | 10 | <1 |
| Sn | 10 | 10 |
| Zn | 10 | <1 |
| Anionic impurities (unit: ppm) | 30 | 110 |

TABLE 6

| Metallic element content (unit: ppb) | Before flowing through | After flowing through |
|---|---|---|
| Ag | 10 | <1 |
| Al | 10 | <1 |
| Au | 10 | <1 |
| Ca | 10 | <1 |
| Cr | 10 | <1 |
| Cu | 10 | <1 |
| Fe | 10 | <1 |
| K  | 10 | 8 |
| Mg | 10 | <1 |
| Na | 10 | 8 |
| Sn | 10 | <1 |
| Zn | 10 | <1 |
| Anionic impurities (unit: ppm) | 30 | <1 |

TABLE 7

| Metallic element content (unit: ppb) | Before flowing through | After flowing through |
|---|---|---|
| Ag | 10 | <1 |
| Al | 10 | <1 |
| Au | 10 | <1 |
| Ca | 10 | 3 |
| Cr | 10 | 6 |
| Cu | 10 | <1 |
| Fe | 10 | <1 |
| K  | 10 | <1 |
| Mg | 10 | <1 |
| Na | 10 | <1 |
| Sn | 10 | <1 |
| Zn | 10 | <1 |
| Anionic impurities (unit: ppm) | 30 | <1 |

TABLE 8

| Metallic element content (unit: ppb) | Before flowing through | After flowing through |
|---|---|---|
| Ag | 10 | 10 |
| Al | 10 | 2 |
| Au | 10 | 10 |
| Ca | 10 | 3 |
| Cr | 10 | 6 |
| Cu | 10 | <1 |
| Fe | 10 | 10 |
| K  | 10 | <1 |
| Mg | 10 | <1 |
| Na | 10 | <1 |
| Sn | 10 | 10 |
| Zn | 10 | <1 |
| Anionic impurities (unit: ppm) | 30 | 120 |

TABLE 9

| Metallic element content (unit: ppb) | Before flowing through | After flowing through |
|---|---|---|
| Ag | 10 | <1 |
| Al | 10 | <1 |
| Au | 10 | <1 |
| Ca | 10 | <1 |
| Cr | 10 | <1 |
| Cu | 10 | <1 |
| Fe | 10 | <1 |
| K  | 10 | 7 |
| Mg | 10 | <1 |
| Na | 10 | 7 |
| Sn | 10 | <1 |
| Zn | 10 | <1 |
| Anionic impurities (unit: ppm) | 30 | <1 |

TABLE 10

| Metallic element content (unit: ppb) | Before flowing through | After flowing through |
|---|---|---|
| Ag | 10 | <1 |
| Al | 10 | <1 |
| Au | 10 | <1 |
| Ca | 10 | 2 |
| Cr | 10 | 5 |
| Cu | 10 | <1 |
| Fe | 10 | <1 |
| K | 10 | <1 |
| Mg | 10 | <1 |
| Na | 10 | <1 |
| Sn | 10 | <1 |
| Zn | 10 | <1 |
| Anionic impurities (unit: ppm) | 30 | <1 |

INDUSTRIAL APPLICABILITY

In the high-purity carboxylic acid ester provided by the present invention, metal impurities and anionic impurities are highly reduced, and therefore it is industrially useful. The carboxylic acid ester is a compound useful for a wide range of applications such as synthetic raw materials, cleaning agents for electronic components and solvents for paints, adhesives and the like, or as a treatment agent for cleaning of a semiconductor substrate, etching, development of a photoresist and the like in the production of integrated circuits and large-scale integrated circuits.

The invention claimed is:

1. A method for producing a high-purity carboxylic acid ester, the method comprising:
    contacting a first carboxylic acid ester composition that contains anionic impurities and at least silver, aluminum, gold, calcium, copper, iron, potassium, magnesium, sodium, tin, and zinc as metal impurities with a first weakly basic anion-exchange resin to obtain a second carboxylic acid ester composition;
    contacting the second carboxylic acid ester composition with a strongly acidic cation-exchange resin to obtain a third carboxylic acid ester composition; and
    contacting the third carboxylic acid ester composition with a second weakly basic anion-exchange resin to obtain the high-purity carboxylic acid ester,
    wherein:
        an amount of the silver, the aluminum, the gold, the calcium, the chromium, the copper, the iron, the potassium, the magnesium, the sodium, the tin, and the zinc metal impurities in the high-purity carboxylic acid ester is each less than 1 ppb, and
        an amount of the anionic impurities in the high-purity carboxylic acid ester is less than 1 ppm.

2. The method according to claim 1, wherein the carboxylic acid ester is at least one selected from the group consisting of propyl lactate, methyl α-hydroxyisobutyrate, ethyl α-hydroxyisobutyrate, propyl α-hydroxyisobutyrate, butyl α-hydroxyisobutyrate, methyl β-hydroxyisobutyrate, ethyl β-hydroxyisobutyrate, propyl β-hydroxyisobutyrate, and butyl β-hydroxyisobutyrate.

3. The method according to claim 1, wherein the first carboxylic acid composition comprises at least 8 ppb of each of the silver, the aluminum, the gold, the calcium, the chromium, the copper, the iron, the potassium, the magnesium, the sodium, the tin, and the zinc metal impurities.

4. The method according to claim 1, wherein the first carboxylic acid ester composition comprises at least 20 ppm of anionic impurities.

5. The method according to claim 1, wherein the strongly acidic cation-exchange resin comprises a sulfonic acid group.

6. The method according to claim 1, wherein each of the contacting the first carboxylic acid ester composition with the first weakly basic anion-exchange resin, the contacting the second carboxylic acid ester composition with the strongly acidic cation-exchange resin, and the contacting the third carboxylic acid ester composition with the second weakly basic anion-exchange resin occur at 100° C. or lower.

7. The method according to claim 1, wherein:
    the first and second weakly basic anion-exchange resins and the strongly acidic cation-exchange resin are each enclosed in separate columns, and
    the first, second, and third carboxylic acid esters are flowed through each of the columns in each of the contactings.

8. The method according to claim 7, wherein the flow through each of the columns has a space velocity of 1 to 50 $Hr^{-1}$.

9. The method according to claim 7, wherein the flow through each of the columns has a space velocity of 10 to 20 $Hr^{-1}$.

* * * * *